United States Patent
Suzuki et al.

(10) Patent No.: US 9,375,257 B2
(45) Date of Patent: Jun. 28, 2016

(54) HIGH-FREQUENCY TREATMENT INSTRUMENT

(75) Inventors: Keita Suzuki, Tokyo (JP); Megumi Kimura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 1136 days.

(21) Appl. No.: 11/471,051

(22) Filed: Jun. 19, 2006

(65) Prior Publication Data

US 2007/0021749 A1   Jan. 25, 2007

(30) Foreign Application Priority Data

Jun. 21, 2005  (JP) .................................. 2005-180364

(51) Int. Cl.
*A61B 18/14* (2006.01)

(52) U.S. Cl.
CPC ......... *A61B 18/1445* (2013.01); *A61B 18/1492* (2013.01); *A61B 2018/1407* (2013.01)

(58) Field of Classification Search
CPC .................. A61B 2018/1407; A61B 18/1445; A61B 18/1492
USPC .......................................... 606/41, 47, 50–52
See application file for complete search history.

(56) References Cited

U.S. PATENT DOCUMENTS

| | | | |
|---|---|---|---|
| 4,632,110 A | 12/1986 | Sanagi | |
| 4,817,630 A | 4/1989 | Schintgen et al. | |
| 4,932,419 A | 6/1990 | de Toledo | |
| 4,951,677 A | 8/1990 | Crowley et al. | |
| 5,052,404 A | 10/1991 | Hodgson | |
| 5,108,411 A | 4/1992 | McKenzie | |
| 5,165,421 A | 11/1992 | Fleischhacker et al. | |
| 5,251,640 A | 10/1993 | Osborne | |
| 5,306,252 A | 4/1994 | Yutori et al. | |
| 5,368,035 A | 11/1994 | Hamm et al. | |
| 5,373,619 A | 12/1994 | Fleischhacker et al. | |
| 5,406,951 A | 4/1995 | ten Hoff et al. | |
| 5,437,282 A | 8/1995 | Koger et al. | |
| 5,438,997 A | 8/1995 | Sieben et al. | |
| 5,482,054 A | 1/1996 | Slater et al. ................... | 128/751 |

(Continued)

FOREIGN PATENT DOCUMENTS

| | | |
|---|---|---|
| DE | 88 08 285 | 9/1988 |
| EP | 1 454 588 | 9/2004 |

(Continued)

OTHER PUBLICATIONS

Letter from German associate dated Dec. 7, 2006 forwarding the Search Report dated Dec. 1, 2006 to Japanese associate, including discussion of relevancy thereof.

(Continued)

*Primary Examiner* — Michael Peffley
*Assistant Examiner* — Samantha Good
(74) *Attorney, Agent, or Firm* — Ostrolenk Faber LLP

(57) ABSTRACT

A high-frequency treatment instrument 1 comprises a flexible tube 3 which is inserted into a body cavity and a treatment portion 2 which is located on the distal end of the flexible tube 3 when a high-frequency current is applied. In this high frequency treatment instrument 1, the flexible tube 3 is formed by a plurality of wound conductive wires and is provided with a multiple-thread coil 6 connected electrically to the treatment portion 2, and the high-frequency current is applied to the multiple-thread coil 6.

6 Claims, 13 Drawing Sheets

(56) References Cited

U.S. PATENT DOCUMENTS

| | | | |
|---|---|---|---|
| 5,501,694 | A | 3/1996 | Ressemann et al. |
| 5,507,296 | A | 4/1996 | Bales et al. |
| 5,524,630 | A | 6/1996 | Crowley |
| 5,609,285 | A | 3/1997 | Grant et al. |
| 5,649,955 | A | 7/1997 | Hashimoto et al. |
| 5,678,296 | A | 10/1997 | Fleischhacker et al. |
| 5,796,044 | A | 8/1998 | Cobian et al. |
| 5,803,812 | A | 9/1998 | Kakiuchi et al. |
| 5,810,887 | A | 9/1998 | Accorti, Jr. et al. |
| 5,816,923 | A | 10/1998 | Milo et al. |
| 5,893,885 | A * | 4/1999 | Webster, Jr. .................. 607/122 |
| 6,015,381 | A | 1/2000 | Ouchi |
| 6,027,460 | A | 2/2000 | Shturman |
| 6,027,522 | A | 2/2000 | Palmer |
| 6,078,830 | A * | 6/2000 | Levin et al. ................... 600/374 |
| 6,129,683 | A | 10/2000 | Sutton et al. |
| 6,210,395 | B1 | 4/2001 | Fleischhacker et al. |
| 6,273,860 | B1 | 8/2001 | Kostylev et al. |
| 6,344,037 | B1 | 2/2002 | Suorsa et al. |
| 6,364,846 | B1 | 4/2002 | Nakamura |
| 6,409,727 | B1 * | 6/2002 | Bales et al. ..................... 606/47 |
| 6,419,644 | B1 | 7/2002 | White et al. |
| 6,443,909 | B1 | 9/2002 | Ouchi |
| 6,522,930 | B1 * | 2/2003 | Schaer et al. ................. 607/101 |
| 6,792,663 | B2 | 9/2004 | Krzyzanowski |
| 6,818,001 | B2 | 11/2004 | Wulfman et al. |
| 6,881,194 | B2 | 4/2005 | Miyata et al. |
| 7,117,703 | B2 | 10/2006 | Kato et al. |
| 7,588,545 | B2 | 9/2009 | Cohen et al. |
| 7,815,658 | B2 | 10/2010 | Murakami |
| 2001/0052721 | A1 | 12/2001 | Tanaka |
| 2002/0062124 | A1 | 5/2002 | Keane |
| 2002/0177772 | A1 * | 11/2002 | Altman et al. ................ 600/431 |
| 2003/0139689 | A1 | 7/2003 | Shturman et al. |
| 2003/0139750 | A1 | 7/2003 | Shinozuka et al. |
| 2003/0236549 | A1 | 12/2003 | Bonadio et al. |
| 2004/0068291 | A1 | 4/2004 | Suzuki |
| 2004/0243108 | A1 | 12/2004 | Suzuki |
| 2005/0004432 | A1 | 1/2005 | Suzuki et al. |
| 2006/0229644 | A1 | 10/2006 | Kortenbach |
| 2007/0255311 | A1 | 11/2007 | Hiraoka |
| 2008/0194910 | A1 * | 8/2008 | Miyamoto et al. ............ 600/104 |
| 2008/0195143 | A1 * | 8/2008 | Suzuki ........................... 606/205 |
| 2010/0228150 | A1 | 9/2010 | Zimmerman et al. |

FOREIGN PATENT DOCUMENTS

| | | |
|---|---|---|
| EP | 1 491 153 | 12/2004 |
| JP | 55-109501 | 7/1980 |
| JP | 63-154173 | 6/1988 |
| JP | 10-507959 | 8/1998 |
| JP | 2000-229084 | 8/2000 |
| JP | 2000-333970 | 12/2000 |
| JP | 2002-102245 | 4/2002 |
| JP | 2004-119961 | 4/2004 |
| JP | 2004-261463 | 9/2004 |
| JP | 2005-058344 | 3/2005 |
| JP | 2005-322792 | 11/2005 |
| JP | 2006-093414 | 4/2006 |
| JP | 2008-194068 | 8/2008 |
| JP | 4526544 | 8/2008 |
| WO | WO 96/36289 | 11/1996 |
| WO | WO 97/07835 | 3/1997 |
| WO | WO 2006/114952 | 11/2006 |

OTHER PUBLICATIONS

Search Report issued by European Patent Office on Dec. 1, 2006 in connection with corresponding European patent application No. EP 06 01 2569.

Office Action issued by the Japanese Patent Office on Mar. 15, 2011 in connection with corresponding Japanese Patent Application No. 2005-180364.

Translation of the Office Action issued by the Japanese Patent Office on Mar. 15, 2011 in connection with corresponding Japanese Patent Application No. 2005-180364.

Office Action issued by the Japanese Patent Office on Jun. 7, 2011 in connection with corresponding Japanese Patent Application No. 2006-181179 and English Translation thereof.

Office Action issued by the Japanese Patent Office on Apr. 12, 2011 in connection with corresponding Japanese Patent Application No. 2006-199286 and English Translation thereof.

Office Action issued on Sep. 1, 2010 in U.S. Appl. No. 12/027,515.

Office Action issued on Sep. 2, 2010 in U.S. Appl. No. 12/026,881.

European Search Report mailed Dec. 3, 2010 in corresponding European Application No. 10009961.3-2305.

Office Action issued by the Japanese Patent Office on Jan. 31, 2012 in connection with corresponding Japanese Patent Application No. 2007-119384.

Translation of Office Action issued by the Japanese Patent Office on Jan. 31, 2012 in connection with corresponding Japanese Patent Application No. 2007-119384.

Office Action issued by USPTO on Apr. 13, 2011 in connection with corresponding U.S. Appl. No. 12/026,881.

European Search Report mailed Jan. 22, 2010 in corresponding European Application No. EP 08 002 196.7.

Japanese Office Action issued May 25, 2010 in connection with corresponding Japanese application No. 2007-029053.

Office Action issued by U.S. Patent Office on Dec. 23, 2014 in connection with corresponding U.S. Appl. No. 12/027,515.

Office Action issued by U.S. Patent Office on Jun. 29, 2015 in connection with corresponding U.S. Appl. No. 12/027,515.

\* cited by examiner

HIGH-FREQUENCY TREATMENT INSTRUMENT

BACKGROUND OF THE INVENTION

1. Field of the Invention

The present invention relates to a high-frequency treatment instrument which is used with an endoscope and used in various treatments. Priority is claimed on Japanese Patent Application No. 2005-180364 filed on Jun. 21, 2005, the content of which is incorporated herein by reference.

2. Description of the Related Art

In recent years, high-frequency treatment instruments, which are used with endoscopes to check monitored images, are used in the medical field or the like for various treatments. These high-frequency treatment instruments generally comprises a flexible tube provided with a coiled body, an operative wire movably inserted through the flexible tube and a treatment portion located on the operative wire where a high-frequency current sent from a high-frequency power source is applied.

It is well known to apply the high-frequency current to the operative wire and to apply the high-frequency current to the treatment portion via the operative wire (refer, for example, to Japanese Unexamined Patent Application, First Publication No. 2005-58344).

It is also proposed to wind a wire rod for creation a short circuit around the circumference of the coiled body and to apply the high-frequency current to the wire rod and in turn apply it to the treatment portion (refer, for example, to Japanese Unexamined Patent Application, First Application No. 2000-333970).

SUMMARY OF THE INVENTION

It is preferable to decrease the impedance against the high-frequency current as much as possible in order to apply the high-frequency current sent from the high-frequency power source to the treatment portion efficiently.

The high-frequency treatment instrument according to the present invention comprises a flexible tube which is inserted into the body cavity and a treatment portion located on the distal end of the flexible tube where the high-frequency current is applied. The flexible tube of the high-frequency treatment instrument is made of a plurality of wound conductive wires and is provided with a multiple-thread coil connected electrically to the treatment portion. The high-frequency current is applied to the multiple-thread coils.

With this high frequency treatment instrument, when the high-frequency current is applied to the multiple-thread coils, the high-frequency current is then applied to the treatment portion via the multiple-thread coils.

Here, since the multiple-thread coil is made of a plurality of wound conductive wires, the total cross section of the conductive wires is larger than that of a single-thread coil by the increase in the number of the conductive wires. Furthermore, since each conductive wire is wound such that a space is reserved for other conductive wires, the length of the multiple-thread coil wound from its proximal end to its distal end becomes shorter. As a result, it is possible to decrease the impedance of the multiple-thread coil against the high-frequency current without providing a wire rod in the radial direction of the multiple-thread coil.

Preferably, one of the conductive wire of the plurality of conductive wires provided in the above-described high-frequency treatment instrument, a first wire is made of a material that has a higher conductivity than that of a second wire and the second conductive wire is made of a material that has superior mechanical characteristics than that of the first wire.

Preferably, the plurality of conductive wires of the above-mentioned high-frequency treatment instruments is provided with a conductive member covering the plurality of conductive wires.

Preferably, the above-mentioned high-frequency treatment instruments are provided with an operative wire which is movably inserted through the flexible tube and electrically connected to the treatment portion. The high-frequency current is then applied to both the multiple-thread coil and the operative wire.

Preferably, the high-frequency treatment instrument according to the present invention comprises the flexible tube which is inserted into the body cavity, the operative wire which is movably inserted into the flexible wire, and the treatment portion which is electrically connected to the operative wire and to which the high-frequency current is applied. With this high-frequency treatment instrument, the operative wire comprises a plurality of materials in which a first material has higher conductivity than the other and a second material has superior mechanical characteristics than the first material, where the high-frequency current is applied to the above-described operative wire.

Preferably, the high-frequency treatment instrument according to the present invention is provided with the operative wire comprising a first wire made of the first material and a second wire made of the second material.

Preferably, the high-frequency treatment intent according to the present invention is provided with the operative wire comprising the first wire and the second wire which are twisted together.

Preferably, the high-frequency treatment instrument according to the present invention is provided with the operative wire comprising the first wire and the second wire which are located in parallel with each other.

Preferably, the high-frequency treatment instrument according to the present invention is provided with the operative wire comprising the first wire and the second wire which are connected in the longitudinal direction with each other.

Preferably, the high-frequency treatment instrument according to the present invention is provided with the operative wire comprising a core wire made of the second material and a conductive member made of the first material and covering the core wire.

Preferably, the high-frequency treatment instrument according to the present invention is provided with the operative wire comprising a plastic portion made of the second material which is elongated and a carbon fiber made of the first material provided inside of the plastic portion, which is extended along the whole length of the plastic portion.

Preferably, the high-frequency treatment instrument according to the present invention comprises the flexible tube, which is formed by a wound conductive wire, and a coiled body which is electrically connected to the treatment portion, and the high-frequency current is applied to both the coiled body and the operative wire.

Preferably, the high-frequency treatment instrument according to the present invention comprises the flexible tube, which is inserted into the body cavity, and the treatment portion located on the distal end of the flexible tube where the high-frequency current is applied. The flexible tube of the high-frequency treatment instrument is formed with the twisted conductive wire covered by the conductive member and is provided with a coiled body which is electrically connected to the treatment portion, and the high-frequency current is applied to the coiled body.

DETAILED DESCRIPTION OF THE INVENTION

Figure 1:
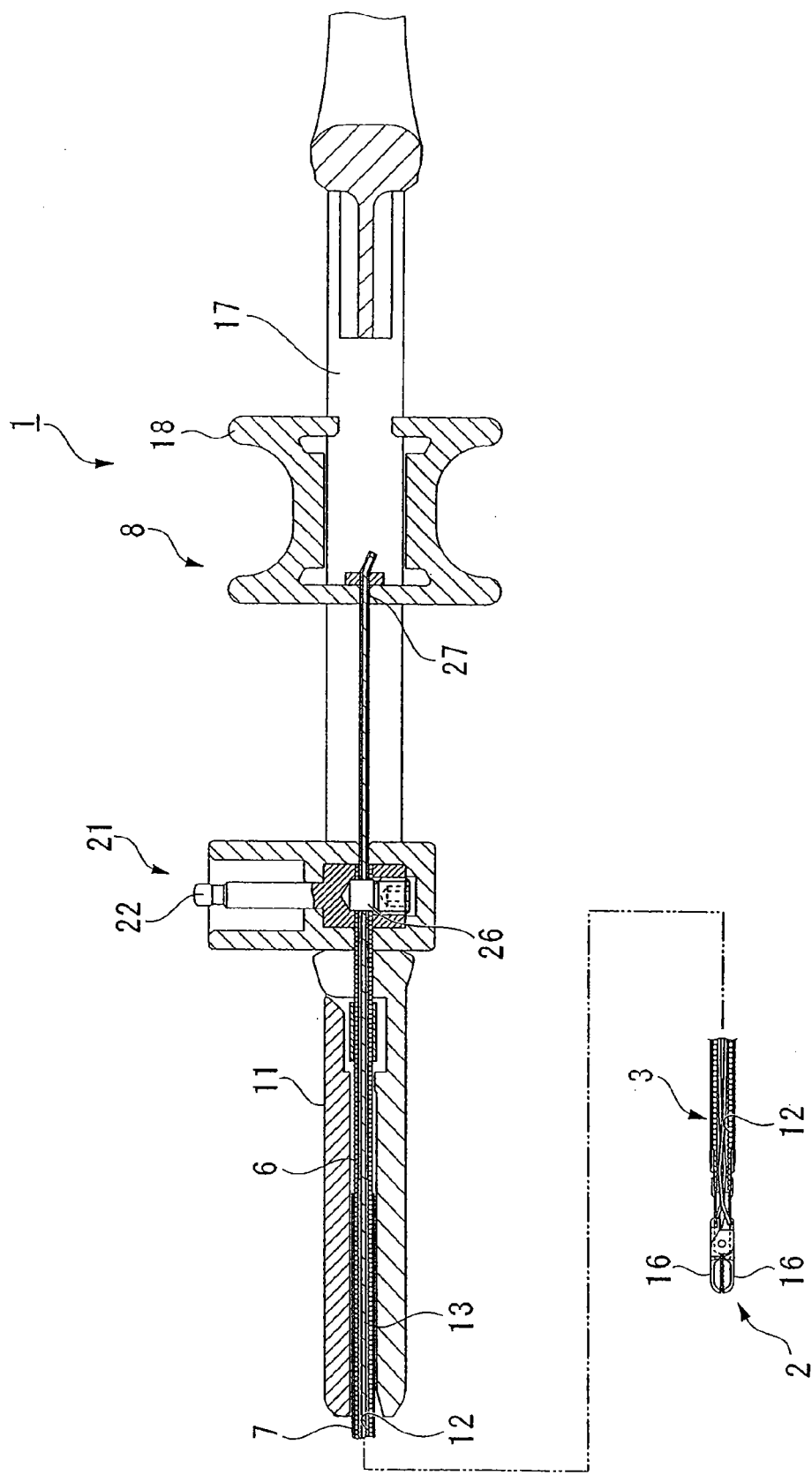
FIG. 1 is a sectional side view of a first embodiment of a high-frequency treatment instrument according to the present invention.

The best mode for cling out the invention is explained by referring to the drawings.

Embodiment 1

First, a first embodiment of the present invention is explained.

Reference symbol 1 in FIG. 1 shows a high-frequency treatment instrument.

Figure 2:
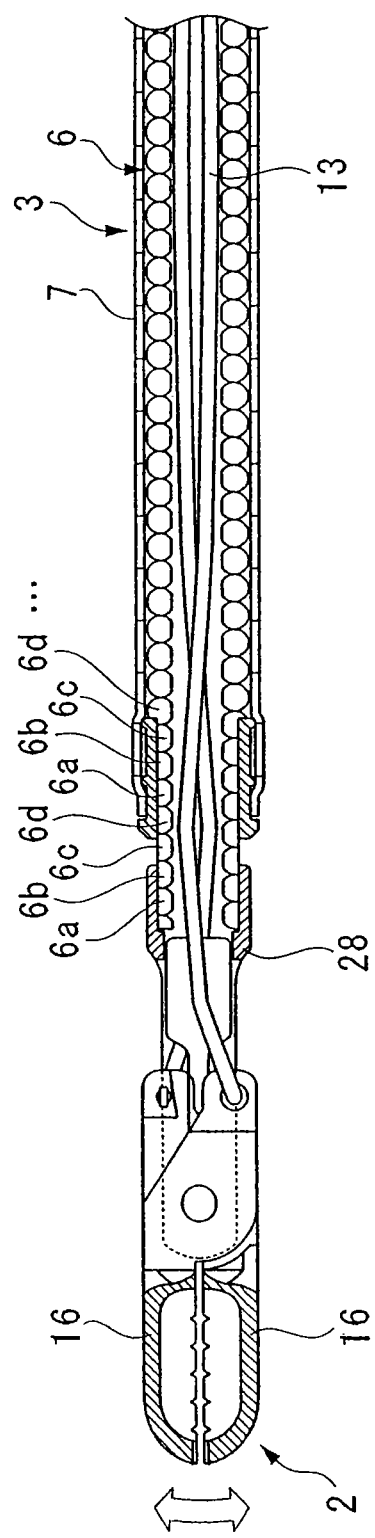
FIG. 2 is a partially enlarged sectional side view of a treatment portion and a sheath portion of FIG. 1.
Figure 3:
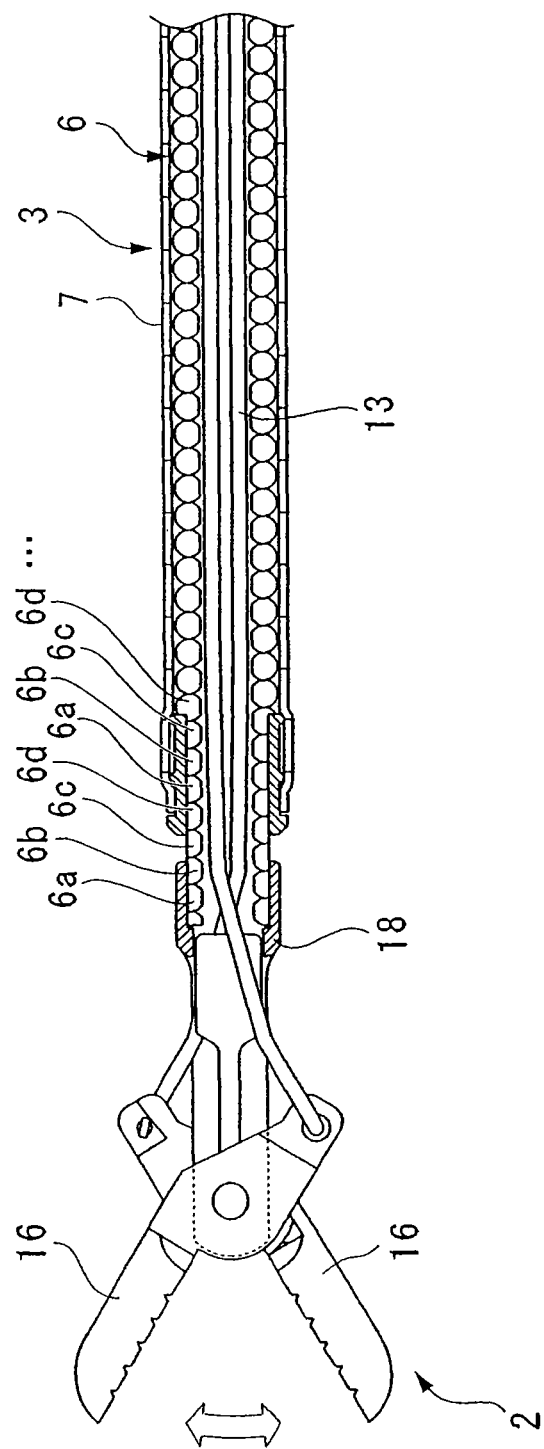
FIG. 3 is an explanatory figure for a state where a pair of jaws shown in FIG. 2 is open.

The high-frequency treatment instrument 1 is provided with a sheath portion 3 (a flexible tube) which is flexible and cylindrically extended. The sheath portion 3 is provided with a multiple-thread coil, which is explained later, and an outer tube 7 is provided around the circumference of the multiple-thread coil covering the circumference of the multiple-thread coil. An operative wire 13 is inserted through the multiple-thread coil 6 which forms the cylindrical hole 12 of the sheath portion 3. The operative wire 13 is made of a metal wire such as stainless steel or steel which has superior mechanical characteristics and is movable forward and backward with respect to sheath portion 3. A treatment portion 2, which is provided with a pair of jaws 16, is provided on the distal end of the sheath portion 3. The distal end of the operative wire 13 is connected to the proximal end of the pair of jaws 16. When the operative wire 13 is moved forward and backward with respect to the sheath portion 3, the pair of jaws 16 opens and closes as shown in FIG. 2 and FIG. 3.

An operative portion 8, which is used to perform various operations, is connected to the proximal end of the sheath portion 3.

The operative portion 8 comprises a distal operative portion 11 to which the sheath portion 3 is connected, an operative main body 17, which extends from the distal operative portion 11 in the proximal direction along the axis of the sheath 3, and a sliding portion 18, which is inserted by the operative main body and is movable forward and backward with respect to the operative main body 17. A connection portion 21, which is connected to a high-frequency power source which is not shown in the figures, is provided on the operative main body 17. The connection portion 21 is provided with a cylindrical electrode terminal 22. When a cable which extends from a high-frequency power source is connected to the connecting portion 21, the cable and the electrode terminal 22 are electrically connected. The cable and the high-frequency power source are not shown in the figures.

The proximal end of the operative wire 13 is connected to the sliding portion 18 via a wire attaching portion 27. When the sliding portion 18 is moved forward and backward with respect to the operative main body 17, the operative wire 13 is moved forward and backward with respect to the sheath portion 3.

The sheath portion 3 according to the present embodiment is further provided with the above-described multiple-thread coil 6. As shown in FIG. 2, the multiple-t coil 6 comprises a plurality of conductive wires 6a, 6b, 6c and 6d wound at a certain diameter. The conductive wires 6a, 6b, 6c and 6d are, for example, metal wire made of stainless steel, steel, hard steel, piano wire, copper or copper alloy, silver or silver alloy, platinum or platinum alloy, gold, or the like.

On the distal end of the multiple-thread coil 6, an annular connection portion 28 is provided. On the distal end of the connection portion 28, the treatment portion 2 is further provided. The connection portion 28 is made of a conductive member such as various metals, and the outer surface of the connection portion 28 is insulated. Accordingly, multiple-thread coil 6 and the eminent portion 2 are electrically connected via the connection portion 28.

On the other hand, as shown in FIG. 1, the proximal end of the multiple-thread coil 6 is fixed to a coil attaching portion 26 located on the proximal end of the electrode terminal 22. By attaching the multiple-thread coil 6 to the coil attaching portion 26, each conductive wire 6a, 6b, 6c and 6d is electrically connected to the electrode terminal 22.

Next, a function of the high-frequency treatment instrument 1 according to the present embodiment constituted as above is explained.

First, the insertion portion of an endoscope is inserted into the body cavity and the insertion portion is then sent to the vicinity of the area to be treated. Furthermore, the sheath portion 3 is inserted into the body cavity and then guided to the treated area via a channel for forceps provided at the insertion slot of the endoscope. Next, a cable extending from the high-frequency power source is connected to the connecting portion 21. The sliding portion 18 is moved backward, the pair of jaws 16 is opened, and then the treated area is set between the pair of jaws 16. Next, when the sliding portion is moved forward, the pair of jaws 16 are close and the treated area is pinched. In this state, as explained later, by applying the high-frequency current to the treatment area 2, the treated area is burned in order to stop bleeding or perform dissection.

Here, in this embodiment, the high-frequency current is applied to the treatment area 2 in the following manner. As described above, when the cable extending from the high-frequency power source is connected to the connecting portion 21, the cable and the electrode terminal 22 are electrically connected. As a result, the electrode terminal 22 and the treatment portion 2 electrically connected via the coil attaching portion 26, the multiple-thread coil 6, and the connection portion 28. The high-frequency power source is activated in this connected state. The high-frequency current from the high-frequency power source is then sent from the cable to the electrode terminal 22 and further sent to respective conductive wires 6a, 6b, 6c, and 6d via the coil attaching portion 26.

In this state, since the multiple-thread coil 6 is provided, the number of conductive wires 6a, 6b, 6c, and 6d is increased compared to a single-thread coil formed only by one wire being wound; therefore the whole cross section of the conductive wires 6a, 6b, 6c, and 6d becomes larger. Furthermore, since the conductive wire 6a, for example, is wound such that a space is reserved for the other conductive wire 6b, 6c, and 6d, the length of the conductive wire 6a wound from the distal end to the proximal end of the multiple-thread coil 6 becomes shorter. In a similar way, the length of other conductive wires 6b, 6c, and 6d becomes shorter. The high-frequency current is applied to the treatment portion 2 via the connection portion 28 by passing through the conductive wire 6a, 6b, 6c, and 6d.

As described above, according to the high-frequency treatment instrument 1 of the present embodiment, since the whole cross section of the conductive wire 6a, 6b, 6c, and 6d becomes larger, and since the length of each wire becomes shorter, it is possible to decrease the total impedance between the high-frequency power source and the treatment portion 2 without providing a wire for creating a short circuit in the radial direction on the multiple-thread coil 6. This leads to not only applying the high-frequency current to the treatment portion 2 as efficiently as possible but also makes it possible to maintain the diameter of the sheath 3 and accordingly make prompt and easy treatment possible.

Figure 4:
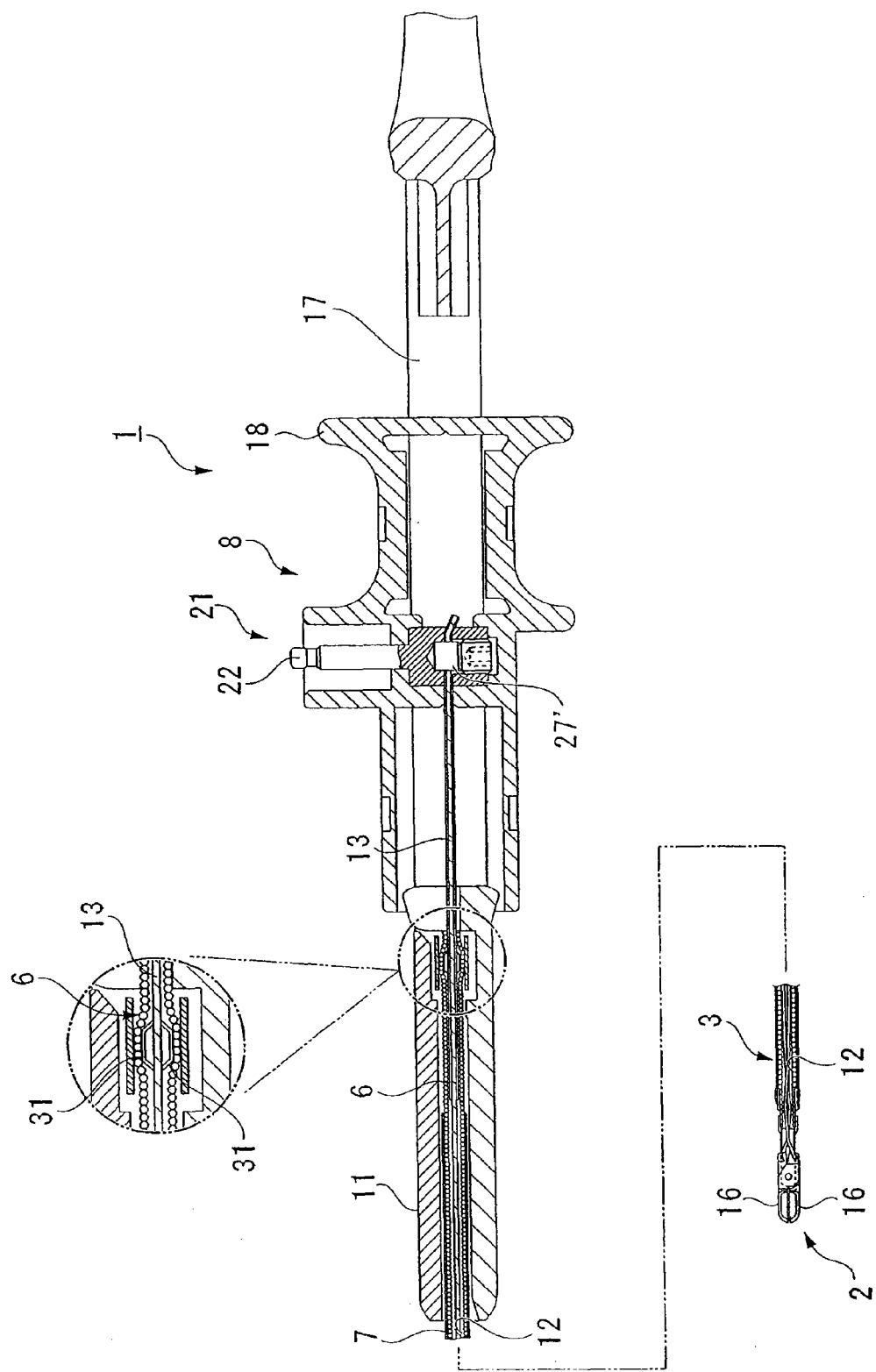
FIG. 4 is a sectional side view of a modified embodiment of the high-frequency treatment instrument in FIG. 1.

The high-frequency treatment instrument 1 according to the present embodiment is constituted so that the high-frequency current is sent to the multiple-rad coil 6, but the constitution is not limited to this embodiment. The high-frequency current may be sent to both the multiple-thread coil 6 and the operative wire 13. As shown in FIG. 4, for example, the connection portion 21 is provided on the sliding portion 18 and a wire attaching portion 27' is provided on the proximal end of the electrode terminal 22. By connecting the operative wire 13 to the wire attaching portion 27', the electrode terminal 22 and the operative wire 13 are electrically connected. Furthermore, a connection piece 31, made of a conductive member, is provided on the circumference of the operative wire 13 and the connection piece 31 where the multiple-tread coil 6 makes contact. The operative wire 13 and the treatment portion 2 are electrically connected. Accordingly, the operative wire 13 and the multiple-thread coil 6 are electrically connected in parallel.

Under this constitution, when the high-frequency power source is activated, the high-frequency current is applied from the electrode terminal 22 to the operative wire 13. A portion of the high-frequency current is applied to the operative wire 13 and the rest of the current is sent to the multiple-thread coil 6 via the connection piece 31. That is, the high-frequency current is sent to both the operative wire 13 and the multiple-thread coil 6 and then applied to the treatment portion 2.

This leads to a further decrease in the total impedance because of the usage of both the multiple-thread coil 6 and the operative wire 13.

If the multiple-thread coil 6 was a single-thread coil, even if the high-frequency current is applied to the operative wire 13 provided with the connection piece 31, the most of the high-frequency current is sent to the operative wire 13 but almost none is sent to the single-thread coil because the impedance of the single-thread coil is extremely large. That is, the total impedance is almost unchanged.

Since the impedance of the multiple-thread coil 6 is decreased in the high-frequency treatment instrument 1, a large portion of the high-frequency current is applied to the multiple-thread coil 6 via the connection piece 31. That is, as described above, by using both the multiple-thread coil 6 and the operative wire 13, the total impedance can be further decreased.

Figure 5:
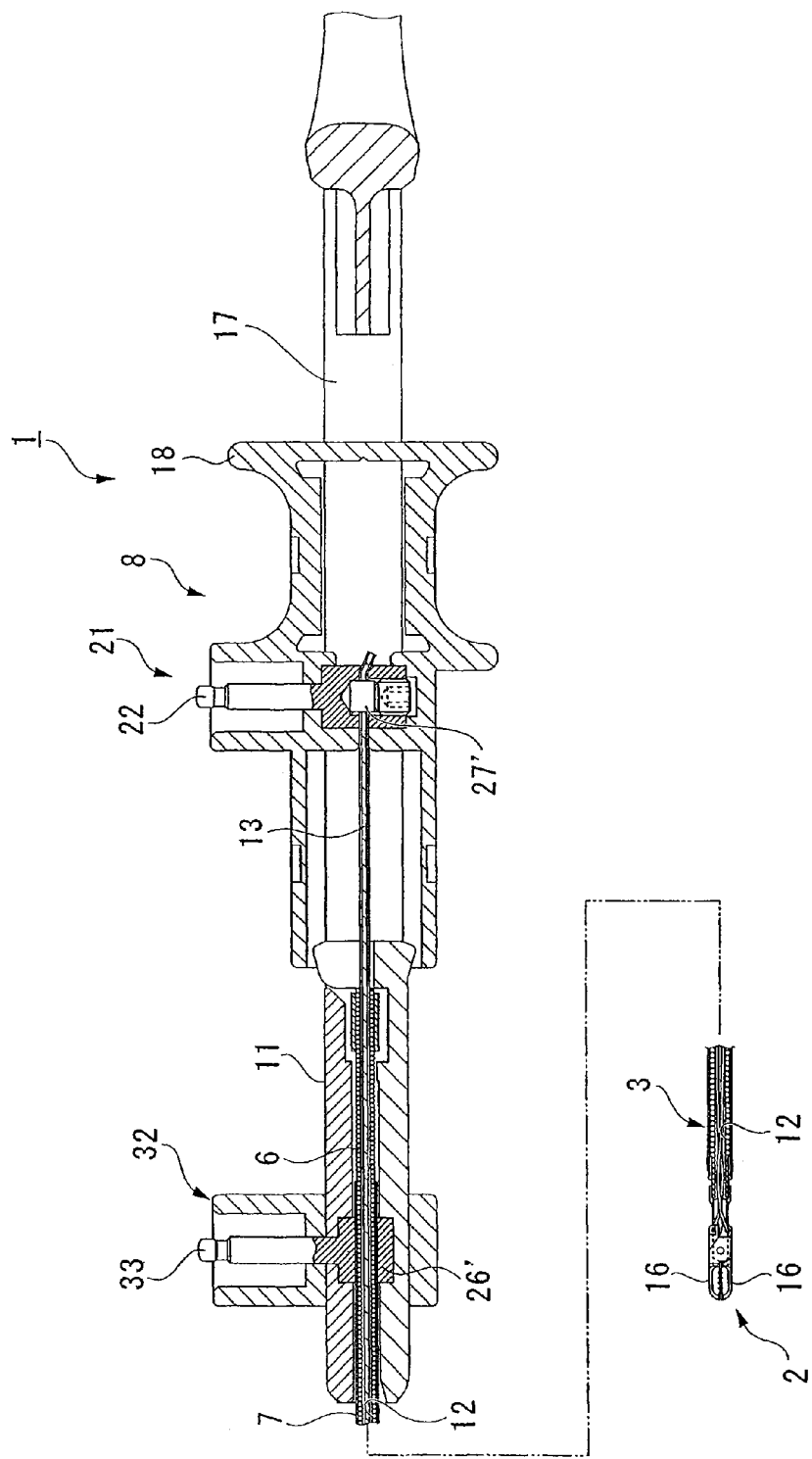
FIG. 5 is a sectional side view of another modified embodiment of the high-frequency treatment instrument in FIG. 1.

As another embodiment for applying the high-frequency current to both the multiple-thread coil 6 and the operative wire 13, a connection portion 32 for the coil may be provided instead of the connection piece 31 as shown in FIG. 5. The multiple-thread coil 6 is attached to the coil attaching portion 26', and an electrode terminal for the coil 33 and the multiple-thread coil 6 are electrically connected. As a result, the multiple-thread coil 6 and the operative wire 13 are electrically connected in parallel via the electrode terminal for the coil 33 and the electrode terminal 22.

Although the plurality of the conductive wires 6a, 6b, 6c, and 6d is described as being made of metal wires, each of the conductive wires may be made of a different material. That is, the conductive wires 6a and 6c may be made of a material with higher conductivity than that of the conductive wires 6b and 6d, and the conductive wires 6b and 6d may be made of a material with superior mechanical characteristics to that of the conductive wires 6a and 6c. For example, the conductive wires 6a and 6c may be metal wires made of such a metal as copper or a copper alloy, silver or a silver alloy, platinum or a platinum alloy, gold or the like, and the conductive wires 6b and 6d may be metal wires made of a metal such as stainless steel, steel, hard steel or the like. That is, the conductive wires 6a and 6c function as the first conductive wire, and the conductive wires 6b and 6d function as the second conductive wire. The pair of the materials which makes up the conductive wires 6a, 6b, 6c, and 6d may be changed if necessary.

Under this constitution, when the high-frequency current is applied to the multiple-thread coil 6, the high-frequency current is mainly applied to the treatment portion 2 by passing through the conductive wires 6a and 6c. Furthermore, mainly due to the conductive wires 6b and 6d, mechanical characteristics necessary for the multiple-thread coil 6, such as tension characteristics or follow-up characteristics against rotation, are secured.

As a result, it is possible to decrease the impedance of the multiple-thread coil 6 while maintaining the mechanical characteristics of the multiple-thread coil 6.

Figure 6:
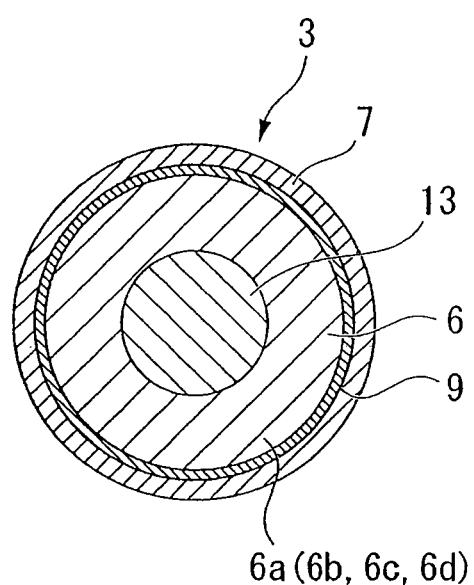
FIG. 6 is a section view showing a multiple-thread coil of FIG. 1 provided with a conductive layer.

Also as shown in FIG. 6, conductive wires 6a, 6b, 6c, and 6d may be provided with a conductive layer (a conductive member) 9 which is made of metal clad or the like. In this case, the multiple-thread coil 6 may be formed after each of the conductive wires 6a, 6b, 6c, and 6d are provided with a conductive layer 9, or the conductive layer 9 may be formed around the whole multiple-thread coil 6 after the multiple-thread coil 6 is formed. As a result, the total impedance can be further decreased. In the case of providing the conductive layer 9, a single-thread coil may be used instead of the multiple-thread coil 6. In this case as well, it is possible to apply the high-frequency current to the conductive layer 9 and the total impedance can be decreased.

Furthermore, although the treatment portion 2 is described as being provided with the pair of jaws 16, other treatment instruments such as a needle scalpel, a snare or a papillotomy knife or the like may be used instead. Although the high-frequency treatment instrument 1 according to the present embodiment is described as being a monopolar type treatment instrument, the treatment instrument is not limited to a monopolar type but it may also be a bipolar type.

Embodiment 2

Next, a second embodiment of the present invention is explained.

Figure 7:
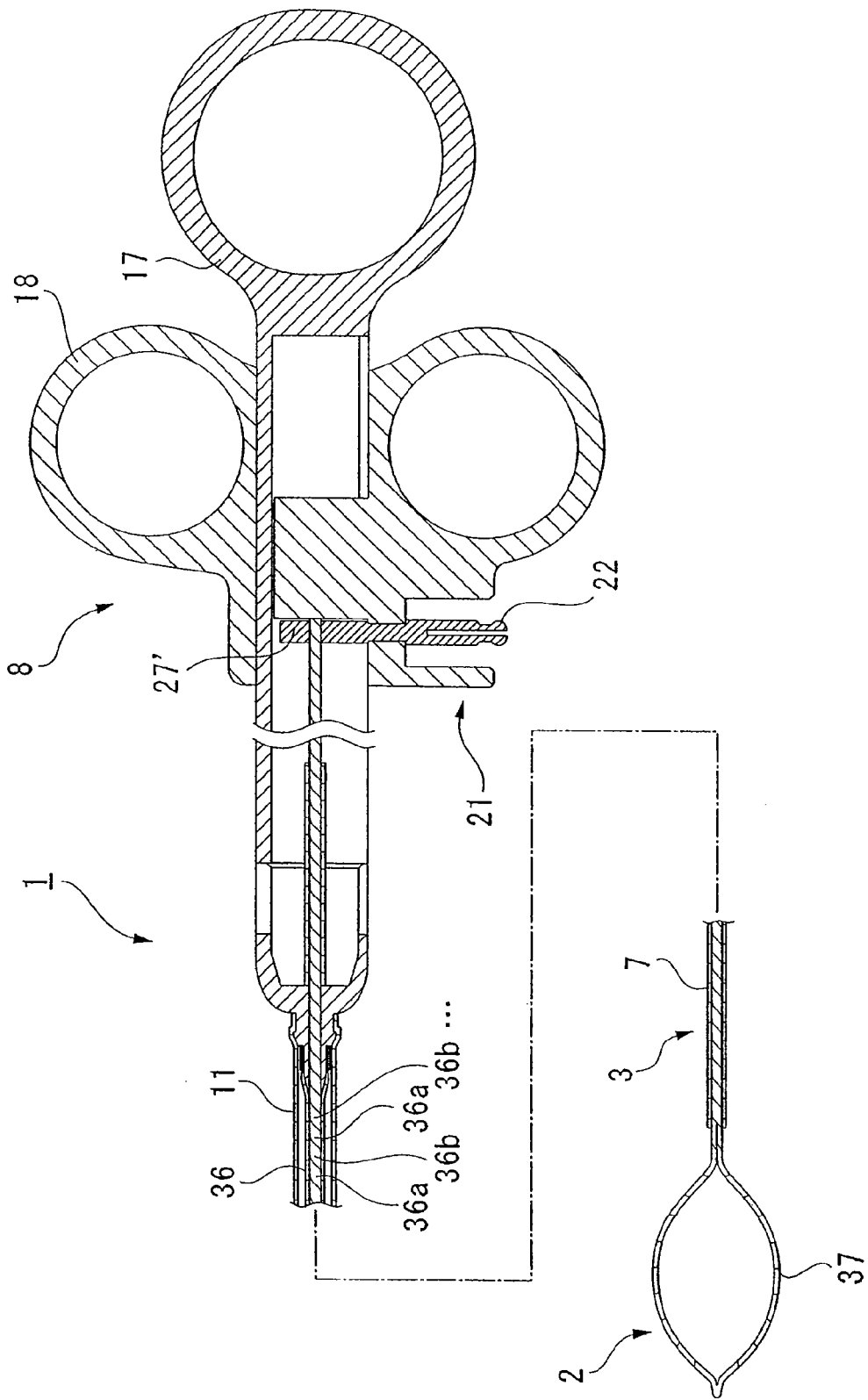
FIG. 7 is a sectional side view of a second embodiment of the high-frequency treatment instrument according to the present invention.
Figure 8:
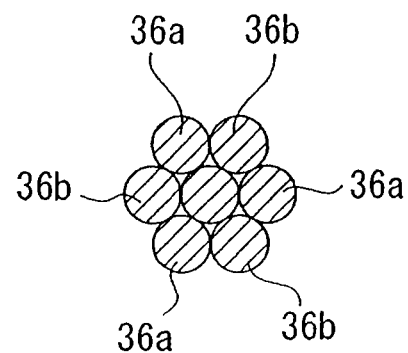
FIG. 8 is an enlarged sectional view of an operative wire of FIG. 7.

FIG. 7 and FIG. 8 show the second embodiment of the present invention.

In FIG. 7 and FIG. 8, the same symbols are provided for the structural members common to the structural members shown in FIG. 1 to FIG. 6 and therefore, those explanations are omitted. The constitution of this embodiment and the above-described first embodiment is basically the same; therefore explanations are made of the points which are not common to the first embodiment.

The high-frequency treatment instrument 1 according to the present embodiment is provided with an operative wire 36 including a first wire 36a and a second wire 36b wherein the operative wire 36 is a thread and the first wire 36a and the second wire 36b are twisted together.

The first wire 36a is made of a material which has a higher conductivity than that of the second wire 36b and the second wire 36b is made of a material which has superior mechanical characteristics than that of the first wire 36a. For example, the first wire 36a is a metal wire made of a material such as copper or a copper alloy, silver or a silver alloy, platinum or a platinum alloy, gold, or the like, and the second wire 36b is a metal wire made of such a material as stainless steel, steel, hard steel or the like.

The treatment portion 2 is constituted as a snare-loop 37 made by a looped elastic wire.

Under this constitution, when the high-frequency current is applied to the operative wire 36, the high-frequency current is also applied to the treatment portion 2 by passing through the fit wire 36a. Because of the second wire 36b, mechanical characteristics necessary for the operative wire 36, such as tension characteristics or follow-up characteristics against rotation are secured.

As a result, it is possible to decrease the total impedance between the high frequency power source and the treatment portion 2 without providing a wire for creating a short circuit in the radial direction on the sheath portion 3. Thus, this constitution not only makes it possible to apply the high-frequency current to the treatment portion 2 efficiently but also, maintains the diameter of the sheath portion 3, makes it possible to keep the patients' burden low, and makes fast and easy treatments possible. Furthermore, it is possible to decrease the impedance of the operative wire 36 and, at the same time, to maintain the mechanical characterstics of the operative wire 36.

Here, as shown in FIG. 8, although six of the first wire 36a and the second wire 36b are provided in total, it is not limited to this example. The numbers of wires may be changed if necessary. In this case, any combination of materials with higher conductivity and superior mechanical characteristics may be changed if necessary.

Figure 9:
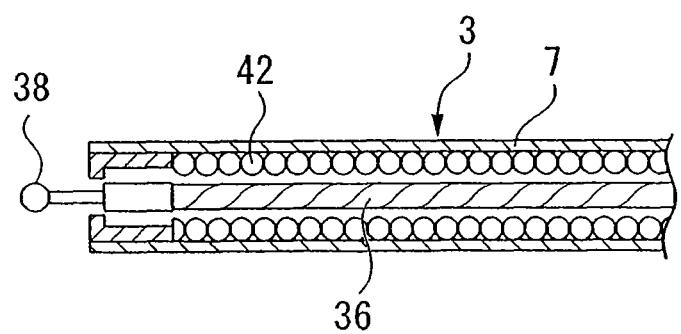
FIG. 9 is a sectional side view of a modified embodiment of the high-frequency treatment instrument in FIG. 7.

Although the treatment portion 2 is described as being a snare-loop 37, it may also be a needle scalpel 38 instead as shown in FIG. 9. Here, reference symbol 42 describes a single-thread coil. Moreover, other treatment instruments such as hemostasis forceps, papillotomy knife, or the like may be used instead.

Embodiment 3

Next a third embodiment of the present invention is explained.

Figure 10:
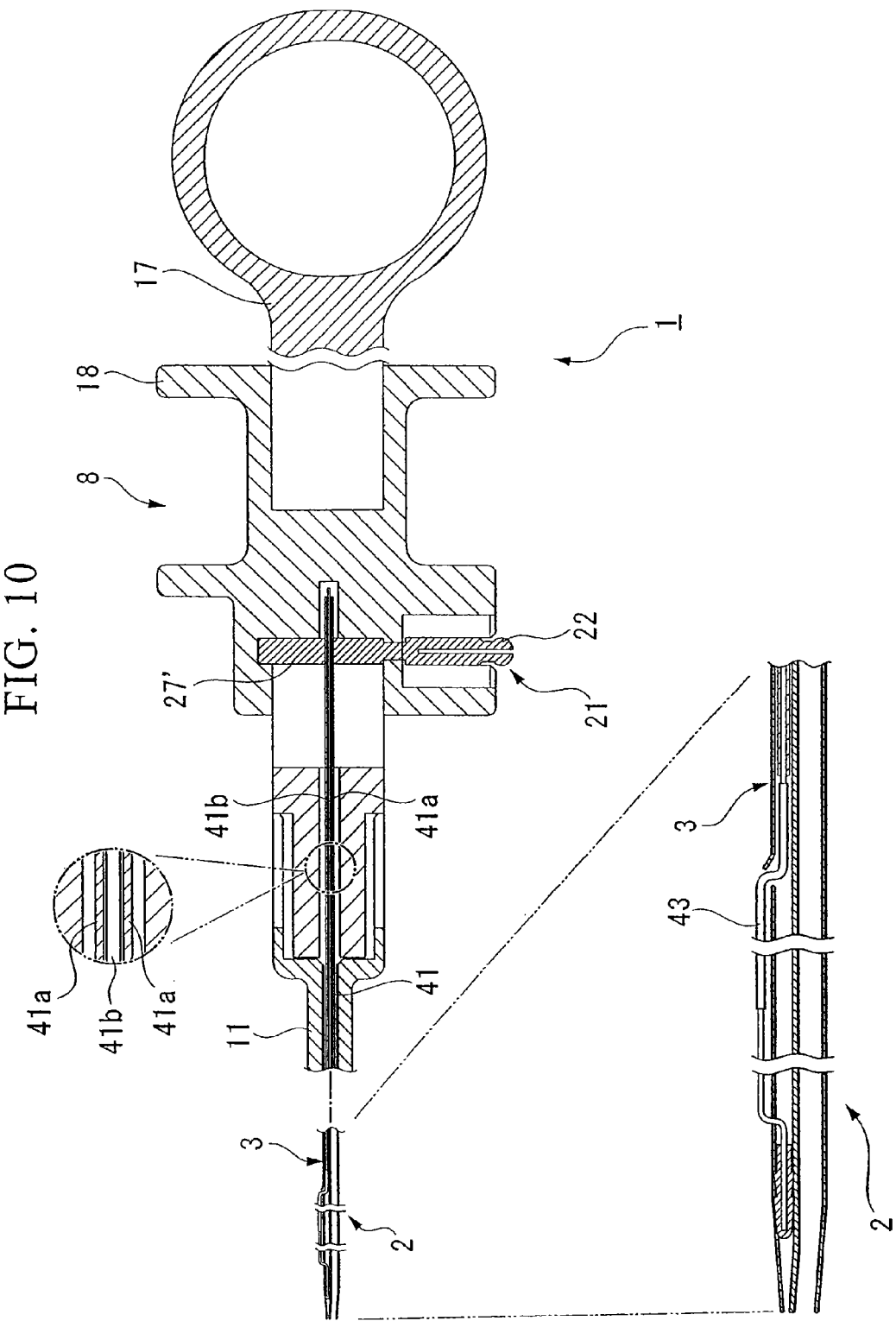
FIG. 10 is a sectional side view of a third embodiment of the high-frequency treatment instrument according to the present invention.
Figure 11:
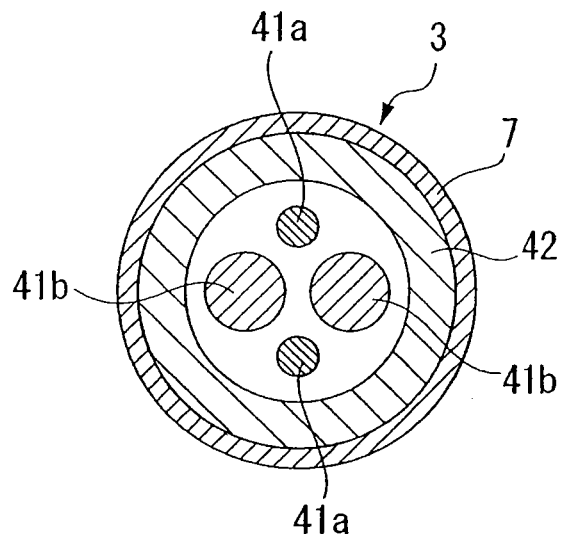
FIG. 11 is an enlarged sectional view of the sheath portion in FIG. 10.

FIG. 10 and FIG. 11 show the third embodiment of the present invention.

An operative wire 41 according to the present embodiment is provided with a first wire 41a with high conductivity and a second wire 41b with superior mechanical characteristics as described above and the first wire 41a and the second wire 41b are located along the axis of the sheath portion 3. That is, the first wire 41a and the second wire 41b are located in parallel with each other.

Here, the treatment portion 2 is provided with a knife 43, and the high frequency treatment instrument 1 is constituted as a papillotomy knife.

Under this constitution, when the high-frequency current is applied to the operative wire 41, the high-frequency current is also applied to the treatment portion 2 by passing through the first wire 41a. The mechanical characteristics necessary for the operative wire 41 are secured by the second wire 41b.

As a result, the same functional effect as the above-described second embodiment can be achieved.

Figure 12:
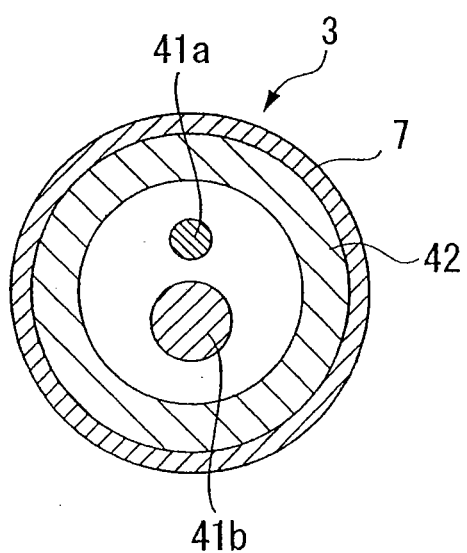
FIG. 12 is a section view showing a modified embodiment of the high-frequency treatment instrument in FIG. 11.

Here, in FIG. 11, although two first wires 41a and two second wires 41b are provided, it is not limited to this example. The number of first wires and the second wires can be changed if necessary. For example, as shown in FIG. 12, one first wire 41a and one second wire 41b may be provided. Because of this, it is possible to make the constitution of the operative wire 41 simple.

Figure 13:
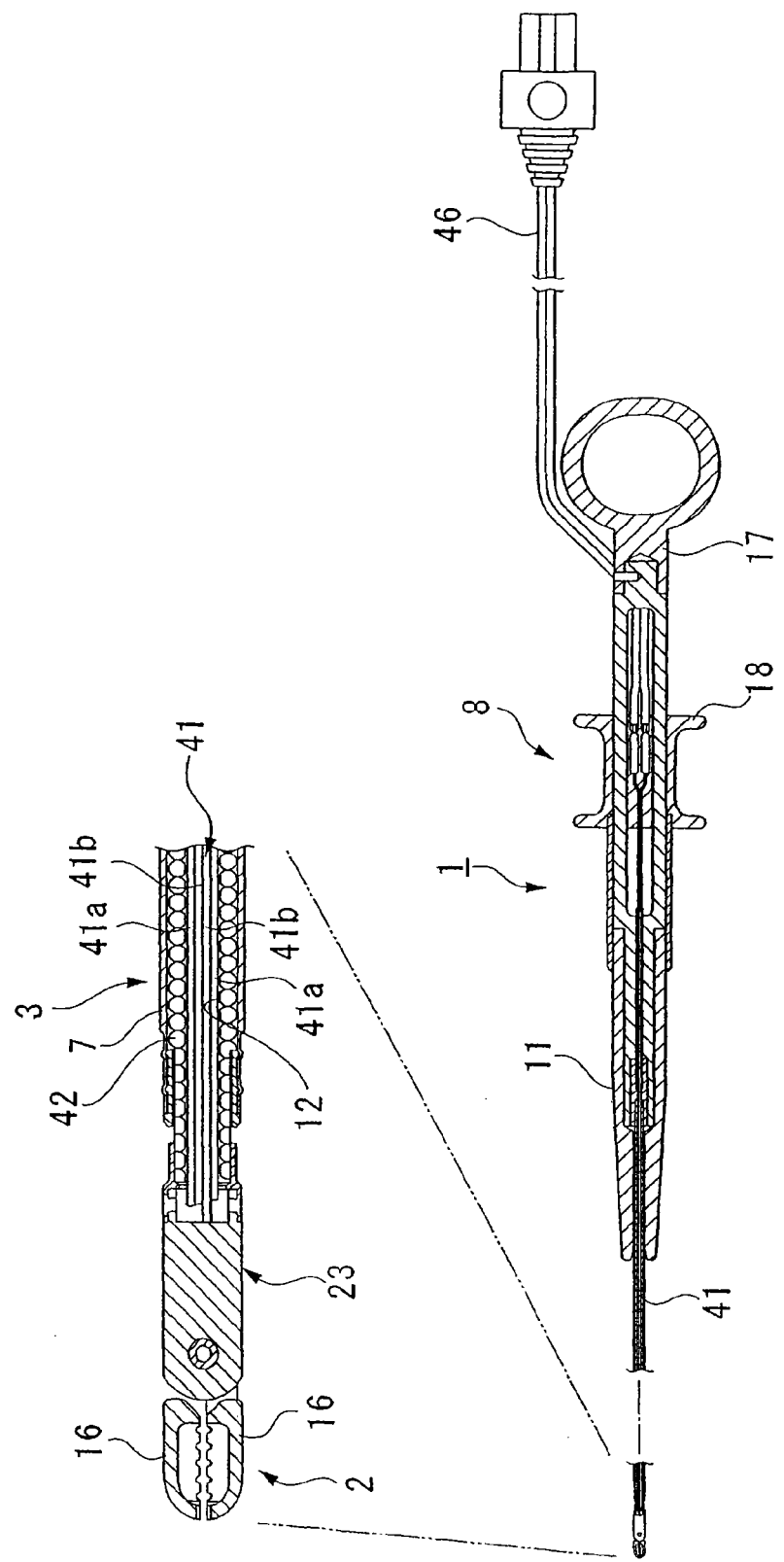
FIG. 13 is a sectional side view of a modified embodiment of the high-frequency treatment instrument in FIG. 10 which is constituted as a bipolar type.

Although, according to the present embodiment, the high frequency treatment instrument 1 is described as being a monopolar type, it may be a bipolar type instead as shown in FIG. 13. In this case, at least two first wires 41a are provided and each of them connected to the negative and positive poles of the cable 46 respectively.

Embodiment 4

Next, a fourth embodiment of the present invention is explained.

Figure 14:
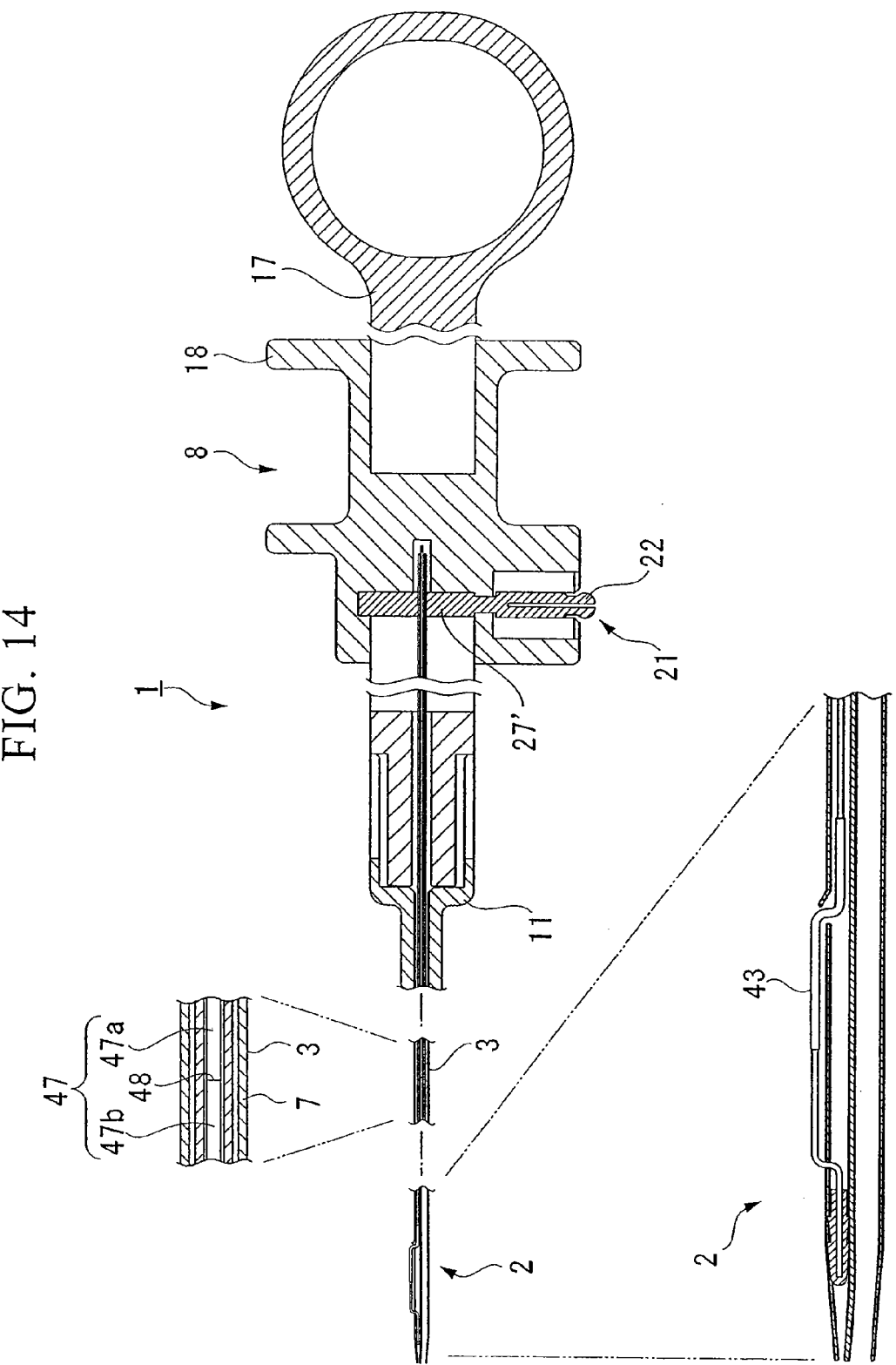
FIG. 14 is a sectional side view of a fourth embodiment of the high-frequency treatment instrument according to the present invention.

FIG. 14 shows the fourth embodiment of the present invention.

An operative wire 47 according to the present embodiment is provided with a first wire 47a with high conductivity as described above and a second wire 41b with superior mechanical characteristics where the first wire 47a and the second wire 47b are connected in the longitudinal direction via a wire connecting portion 48. The first wire 47a is located on the operative portion 8 side and the second wire 47b is located on the treatment portion 2 side.

Furthermore, the knife 43 is constituted such that the second wire 47b is extended.

Under this constitution, when the high-frequency current is applied to the operative wire 47, the high-frequency current is also applied to the treatment portion 2 by passing from the first wire 47a and through the second wire 47b via the wire connecting portion 48. The second wire 47b secures mechanical characteristics necessary for the operative wire 47 such as tension characteristics or torque performance.

Because of this, the same functional effect as that of the second embodiment can be achieved.

Here, in this embodiment, the knife 43 is constituted such that the second wire 47b is extended but it is not limited to this example. The whole second wire 47b may be replaced by a knife 43 and the rest of the wire may be the fit re 47a In this case, the knife 43 is used both as a treatment portion 2 and the operative wire 47.

Also, a needle scalpel or a snare-loop may be provided instead of the knife 43. In this case too, the whole second wire 47b may be replaced by a needle scalpel or a snare-loop. Furthermore, other treatment instruments such as forceps provided with a pair of jaws or the like may be used.

Embodiment 5

Next, a fifth embodiment of the present invention is explained.

Figure 15:
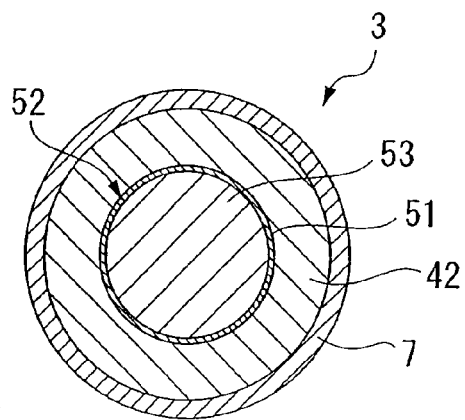
FIG. 15 is a sectional side view of a fifth embodiment of the high-frequency treatment instrument according to the present invention.

FIG. 15 shows the fifth embodiment of the present invention.

An operative wire 52 according to this embodiment is provided with a core wire 53 made of the second material with superior mechanical characteristics and a conductive film (a conductive member) made of the first material with high conductivity. The conductive film 51 is formed on the circumference of the core wire 53 by a metal clad or the like.

Under this constitution, when the high-frequency current is applied to the operative wire 52, the high-frequency current is also applied to the treatment portion 2 by passing through the conductive film 51. Furthermore, the mechanical characteristics are secured because of the core wire 53.

As a result, the same functional effect as that of the second embodiment can be achieved.

Embodiment 6

Next, a sixth embodiment of the present invention is explained.

Figure 16:
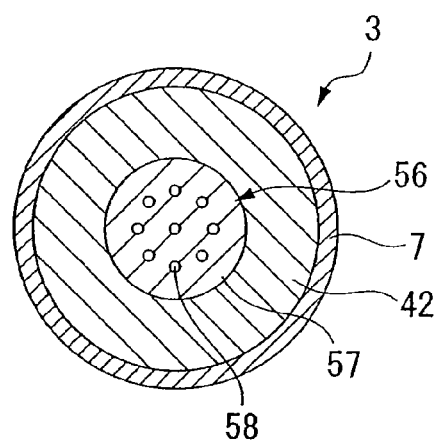
FIG. 16 is a sectional side view of a sixth embodiment of the high-frequency treatment instrument according to the present invention.
Figure 17:
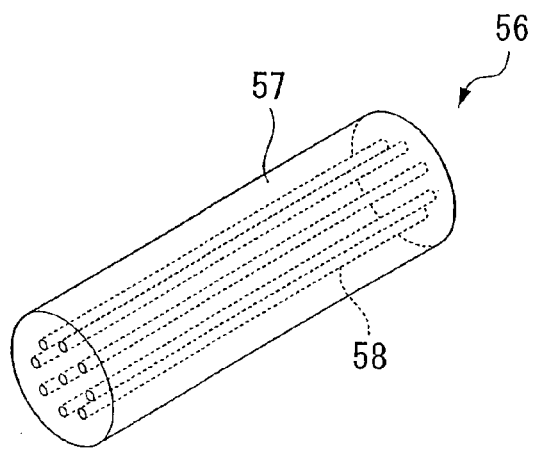
FIG. 17 is an enlarged view explaining an operative wire in FIG. 16.

FIG. 16 and FIG. 17 show the sixth embodiment of the present invention.

An operative wire 56 according to this embodiment is made of a carbon fiber reinforced plastic (CFRP). That is, the operative wire 56 is provided with a plastic portion 57 made of the second material with superior mechanical characteristics and a carbon fiber wire 58 made of the first material with high conductivity. The carbon fiber wire 58 is located inside the plastic portion 57 and extends along the whole length of the plastic portion 57.

Under this constitution, when the high-frequency current is applied to the operative wire 56, the high-frequency current is also applied to the treatment portion 2 by passing through the carbon fiber wire 58. Also, the mechanical characteristics are secured because of the plastic portion 57.

As a result, the same functional effect as that of the second embodiment can be achieved.

Here, in the above-described second to sixth embodiments, although the high-frequency current is applied to the operative wires 36, 41, 47, 52, and 56, it is not limited to this example. The coil member 42 may also be provided and the high-frequency current may be applied to both the coil member 42 and the operative wires 36, 41, 47, 52 and 56. In this case, if the coil member 42 is replaced by the multiple-thread coil, the impedance is further decreased.

With this high-frequency treatment instrument, when the high-frequency current is applied to the multiple-thread coil, the high-frequency current is also applied to the treatment portion by passing through the conductive wire which has a higher conductivity. Furthermore, the tensile strength or the like which is necessary for the multiple-tread coil is secured by the other conductive wire.

Accordingly, it is possible to decrease the impedance of the multiple-thread coil by securing the mechanical characteristics of the multiple-thread coil.

Here, the mechanical characteristics refers to tension characteristics, the bending resistant property, the shear property, torsion characteristics, torque performance, compression characteristics, impact characteristics or the abrasion resistance characteristics or the like.

With this high-frequency treatment instrument, when the high frequency current is applied to the multiple-thread coil, the high-frequency current is also applied to the treatment portion, mainly by passing through the conductive member.

Accordingly, it is possible to further decrease the impedance.

With this high-frequency treatment instrument, the high-frequency current is applied to both the multiple-thread wire and the operative wire, and the high frequency current is applied to the treatment portion by passing through the multiple-sad wire and the operative wire.

Accordingly, it is possible to further decrease the total impedance by implementing the multiple-thread coil and the operative wire.

With this high-frequency treatment instrument, when the high-frequency current is applied to the operative wire, the high-frequency current is also applied to the treatment portion, mainly by passing through the first material with higher conductivity.

Also, due to the second material, the necessary tensile strength or the like for the operative wire are secured.

Accordingly, it is possible to decrease the impedance of the operative wire with securing the mechanical characteristics of the operative wire.

With this high-frequency treatment instrument, when the high-frequency current is applied to the operative wire, the high-frequency current is also applied to the treatment portion by passing through the first wire with higher conductivity. Furthermore, due to the second wire, the necessary tensile strength or the like for the operative wire are secured.

Accordingly, it is possible to decrease the impedance of the operative wire while reliably securing its mechanical characteristics.

These high-frequency treatment instruments have the same effect as the above-described high-frequency treatment instrument which has the operative wire provided with the operative wire comprising a first wire made of the first material and a second wire made of the second material.

With this high-frequency treatment instrument, when the high-frequency current is applied to the operative wire, the high-frequency current is also applied to the treatment portion by passing through the conductive member. Furthermore, due to the core wire, the necessary tensile strength or the like for the operative wire are secured.

Accordingly, it is possible to decrease the impedance of the operative wire while maintaining its mechanical characteristics.

With this high-frequency treatment instrument, when the high-frequency current is applied to the operative wire, the high-frequency current is also applied to the treatment portion by passing through the carbon fiber. Furthermore, due to the plastic portion, the necessary tensile strength or the like for the operative wire are secured.

Accordingly, it is possible to decrease the impedance of the operative wire while maintaining its mechanical characteristics.

With this high-frequency treatment instrument when the high-frequency current is applied to both the coiled body and the operative wire, the high-frequency current is also applied to the treatment portion by passing through the coiled body and the operative wire.

Accordingly, it is possible to further decrease the total impedance due to the coiled body and the operative wire.

With this high-frequency treatment instrument, when the high-frequency current is applied to the coiled body, the high-frequency current is also applied to the treatment portion by passing through the conductive member.

Accordingly, it is possible to decrease the impedance of the coiled body.

According to the invention, because it is possible to decrease the total impedance to the high-frequency current without providing a wire for creating a short circuit in the radial direction of the multiple-thread coil, it is possible not only to apply the high-frequency current to the treatment portion efficiently, blat also to quickly and easily conduct treatments.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A high-frequency treatment instrument comprising:
a flexible tube which is inserted into a body cavity,
a treatment portion which is located on a distal end of the flexible tube, wherein the treatment portion is composed of a pair of forceps pieces capable of opening and closing, and wherein the treatment portion is configured to perform treatment as high-frequency current is being applied to the treatment portion,
a multiple-thread coil which forms the flexible tube, wherein the multiple-thread coil is formed by winding a first conductive wire and a second conductive wire alternatively, wherein the first conductive wire is wound such that a space is reserved for the second conductive wire,
an annular conductive connecting portion provided on a distal end of the multiple-thread coil which holds the pair of forceps pieces wherein the high-frequency current is applied to the multiple-thread coil and is conducted to the conductive connecting portion and applied to each of the pair of forceps pieces through the conductive connecting portion, and
an operative wire which is movably inserted into the multiple-thread coil and the conductive connecting portion to be connected to the forceps pieces so as to operate the forceps pieces,
wherein each of the second conductive wire and the operative wire is formed by winding a metal wire with superior mechanical characteristics relative to the first conductive wire,
the first conductive wire is formed by winding another metal wire with higher conductivity relative to the second conductive wire and the operative wire, and
when the high-frequency current is applied to each of the pair of forceps, a proportion of the high-frequency current passed through the first conductive wire is the largest.

2. The high-frequency treatment instrument according to claim 1, wherein
the operative wire is movable forward and backward and connected electrically to the treatment portion, wherein the high-frequency current is applied to both the multiple-thread coil and the operative wire.

3. The high-frequency treatment instrument according to claim 1 which is made as a monopolar type.

4. The high-frequency treatment instrument according to claim 1, wherein the multiple-thread coil is fixed onto an inner circumferential surface of the flexible tube along the entire length of the multiple-thread coil.

5. The high frequency treatment instrument according to claim 1, wherein
a surface of the conductive connecting portion is insulated.

6. The high frequency treatment instrument according to claim 1, further comprising:
a conductive connection piece which connects the operative wire and the multiple-thread coil.

* * * * *